United States Patent
Jeong et al.

(10) Patent No.: US 11,286,161 B2
(45) Date of Patent: Mar. 29, 2022

(54) PROCESS FOR ISOLATING 17O ISOTOPE FROM WATER AND PROCESS FOR CONCENTRATING 17O ISOTOPE USING THE SAME

(71) Applicant: KOREA ATOMIC ENERGY RESEARCH INSTITUTE, Daejeon (KR)

(72) Inventors: Do-Young Jeong, Daejeon (KR); Lim Lee, Daejeon (KR); Yonghee Kim, Daejeon (KR); Hyounmin Park, Daejeon (KR); Yong-Ho Cha, Daejeon (KR); Taek-Soo Kim, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 564 days.

(21) Appl. No.: 16/290,531

(22) Filed: Mar. 1, 2019

(65) Prior Publication Data
US 2020/0156938 A1     May 21, 2020

(30) Foreign Application Priority Data

Nov. 16, 2018    (KR) .................. 10-2018-0141478
Jan. 11, 2019    (KR) .................. 10-2019-0003990

(51) Int. Cl.
    *C01B 5/02*        (2006.01)
    *C07C 1/04*        (2006.01)
                (Continued)

(52) U.S. Cl.
CPC ............... *C01B 5/02* (2013.01); *B01J 19/121* (2013.01); *C01B 32/40* (2017.08); *C07C 1/0485* (2013.01);
(Continued)

(58) Field of Classification Search
CPC .......... C01B 5/02; C01B 32/40; B01J 19/121; C07C 1/0485
(Continued)

(56) References Cited

U.S. PATENT DOCUMENTS

| | | |
|---|---|---|
| 4,029,559 A | 6/1977 | Marling |
| 5,314,592 A | 5/1994 | Majima et al. |

(Continued)

FOREIGN PATENT DOCUMENTS

| | | |
|---|---|---|
| CN | 101242888 A | 8/2008 |
| CN | 101516476 A | 8/2009 |

(Continued)

*Primary Examiner* — Douglas B Call
(74) *Attorney, Agent, or Firm* — Mintz Levin Cohn Ferris Glovsky and Popeo, P.C.; Peter F. Corless

(57) ABSTRACT

A process for isolating $^{17}O$ from water and a process for concentrating $^{17}O$ by using the same are provided. The process for isolating $^{17}O$ from water includes: mixing $^{17}O$-containing water with formaldehyde to prepare an aqueous formaldehyde solution; heating the aqueous formaldehyde solution to generate a vapor mixture containing water vapor and formaldehyde vapor; and obtaining $^{17}O$-depleted water, residual formaldehyde, and a gas mixture containing hydrogen and $^{17}O$-enriched carbon monoxide, through photodissociating the vapor mixture. An $^{17}O$-enriched water production process includes: an operation of adding hydrogen to the gas mixture to induce a catalytic methanation reaction to synthesize methane ($CH_4$) and $^{17}O$-enriched water ($H_2{}^{17}O$) through methanation, the operation being carried out following the process for isolating $^{17}O$ from water.

11 Claims, 4 Drawing Sheets

(51) Int. Cl.
   *C01B 32/40* (2017.01)
   *B01J 19/12* (2006.01)
(52) U.S. Cl.
   CPC .............. *B01J 2219/0871* (2013.01); *B01J 2219/0875* (2013.01); *B01J 2219/12* (2013.01)
(58) Field of Classification Search
   USPC ..................................................... 423/580.2
   See application file for complete search history.

(56) References Cited

U.S. PATENT DOCUMENTS

| | | | |
|---|---|---|---|
| 2003/0024805 A1 | 2/2003 | Austin | |
| 2003/0183505 A1* | 10/2003 | Austin | ............... C01B 13/0207 204/157.15 |
| 2006/0249366 A1 | 11/2006 | Hayashida | |
| 2009/0035212 A1 | 2/2009 | Kihara et al. | |
| 2009/0266702 A1 | 10/2009 | Kambe et al. | |
| 2014/0301938 A1* | 10/2014 | Jeong | ..................... C07C 45/78 423/461 |

FOREIGN PATENT DOCUMENTS

| | | |
|---|---|---|
| CN | 103055697 A | 4/2013 |
| CN | 103945921 A | 7/2014 |
| JP | S55-86524 A | 6/1980 |
| JP | H1-194932 A | 8/1989 |
| JP | H03-165817 A | 7/1991 |
| JP | H11-94932 A | 4/1999 |
| KR | 10-2013-0058445 A | 6/2013 |
| TW | 200420338 A | 10/2004 |
| WO | 2004035465 A1 | 4/2004 |
| WO | 2007/020934 A1 | 2/2007 |
| WO | WO2013077528 * | 5/2013 |

\* cited by examiner

PROCESS FOR ISOLATING 17O ISOTOPE FROM WATER AND PROCESS FOR CONCENTRATING 17O ISOTOPE USING THE SAME

CROSS-REFERENCE TO RELATED APPLICATIONS

This application claims the benefit of priority to Korean Patent Application No. 10-2018-0141478 filed on Nov. 16, 2018 and Korean Patent Application No. 10-2019-0003990 filed on Jan. 11, 2019 with the Korean Intellectual Property Office, the disclosure of which is incorporated herein by reference in its entirety.

BACKGROUND

1. Field

The present disclosure relates to a process for isolating $^{17}$O from water and a process for concentrating $^{17}$O using the same, and more specifically, to a process for removing $^{17}$O from heavy water or light water by using water as a starting material, and to a process for isolating $^{17}$O from water and concentrating the same.

2. Description of Related Art

Oxygen exists as three stable isotopes in the natural state, $^{16}$O, with the natural abundance of 99.758%, $^{17}$O with the natural abundance of 0.037%, and $^{18}$O with the natural abundance of 0.204%. Here, $^{17}$O-enriched water enriched with $^{17}$O having a nuclear spin of 5/2 to 10% or higher has been used as the raw material for nuclear magnetic resonance (NMR) compounds and as a contrast agent for magnetic resonance imaging (MRI). Such $^{17}$O-enriched waters are quite costly, in that 20% $^{17}$O-enriched water costs about 600 dollars per gram, while 90% $^{17}$O-enriched water costs about 3,500 dollars per gram.

The materials used as moderators in nuclear reactors, namely, graphite, light water ($^{1}$H$_2$O), and heavy water (D$_2$O), contain stable isotopes including $^{17}$O, $^{14}$N, $^{13}$C, and the like, and these isotopes react with neutrons to form a radioactive isotope, $^{14}$C. $^{14}$C has a half-life of 5,730 years and is an organic radionuclide harmful to the human body, and therefore, is a main radionuclide of interest that is strictly regulated in nuclear power plants and radioactive waste treatment sites. Countries in Europe, as well as Canada, the US, and Japan have struggled with the disposal of irradiated graphite produced from gas-cooled reactors and $^{14}$C waste materials produced from heavy water in heavy water reactors. Since the amount of undisposed $^{14}$C currently stored world-wide has reached 500,000 Ci, exceeding the total limit permitted for the entirety of nuclear waste disposal sites, and as relevant regulations have become increasingly more strict, a fundamental reduction of the amount of carbon-14 generated in nuclear reactors is an urgent and pressing matter.

Heavy water (D$_2$O) used as a coolant and moderator in heavy water nuclear reactors contains 0.037-0.059% of $^{17}$O isotope. The amount of $^{14}$C generated from a heavy water nuclear reactor of 1 GWe/yr, which uses about 600 tons of heavy water, has reached 700 Ci per year, wherein 95% or more of this amount is being formed from $^{17}$O contained in the heavy water. Accordingly, reducing the amount of $^{17}$O contained in the heavy water to 1/10 or less may result in reducing the amount of $^{14}$C generated from the heavy water nuclear reactors by 90% or more.

Distillation is known as a commercial technique for isolating oxygen isotopes, such as $^{18}$O and $^{17}$O. Water distillation, a technique which separates water at 320 K, has isotope selectivity for $^{18}$O of about 1.007. Oxygen cryogenic distillation, a technique which isolates oxygen isotopes by distilling liquid oxygen at 90 K, has isotope selectivity for $^{18}$O isotopes of about 1.102. Therefore, it is deemed that reducing the isotopic abundance of $^{17}$O to 0.037% or less, in a cost-effective manner, cannot be achieved by currently available techniques. In the above context, U.S. Pat. No. 8,337,802 B2 has proposed a method that isolates $^{17}$O isotopes through photodissociation of ozone at 160 K by using a near-infrared laser with a wavelength of 998 nm; however, this method has relatively low selectivity for $^{17}$O of about 2.2, and thus may have limited potential as a commercially useful technique.

Accordingly, processes capable of isolating $^{17}$O isotope from water with high selectivity and concentrating the same may be expected to find a wide range of useful applications in related fields.

SUMMARY

An aspect of the present disclosure may provide a process for isolating $^{17}$O from water.

Another aspect of the present disclosure may provide a process for concentrating $^{17}$O using the process for isolating $^{17}$O from water of the present disclosure.

According to an aspect of the present disclosure, a process for isolating $^{17}$O from water may include: preparing an aqueous formaldehyde solution by mixing $^{17}$O-containing water with formaldehyde; preparing a vapor mixture containing water vapor and formaldehyde vapor by heating the aqueous formaldehyde solution; and photodissociating the vapor mixture to obtain a gas mixture containing hydrogen and $^{17}$O-enriched carbon monoxide, $^{17}$O-depleted water, and residual formaldehyde.

According to another aspect of the present disclosure, a process for producing $^{17}$O-enriched water may include: an operation of obtaining a gas mixture containing hydrogen and $^{17}$O-enriched carbon monoxide, $^{17}$O-depleted water, and residual formaldehyde, from $^{17}$O-containing water by the process for isolating $^{17}$O from water of the present disclosure; and a catalytic methanation operation of adding hydrogen to the gas mixture to induce a catalytic methanation reaction to synthesize methane (CH$_4$) and $^{17}$O-enriched water (H$_2$$^{17}$O) through methanation.

BRIEF DESCRIPTION OF DRAWINGS

The above and other aspects, features, and advantages of the present disclosure will be more clearly understood from the following detailed description, taken in conjunction with the accompanying drawings, in which.

DETAILED DESCRIPTION

Figure 1:
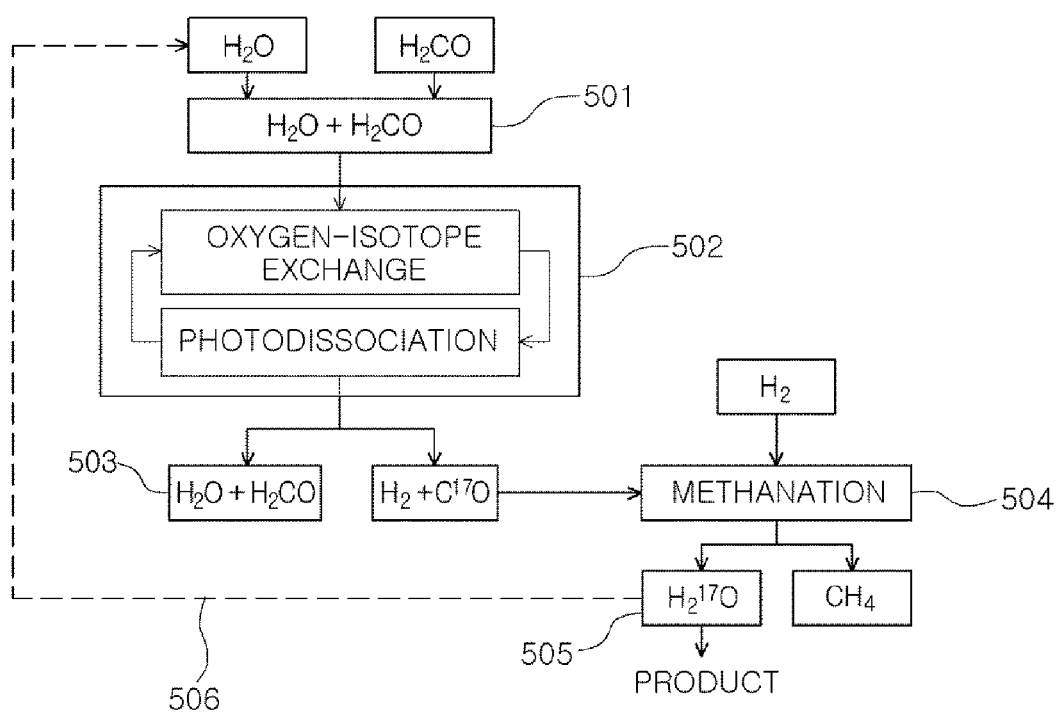
FIG. 1 schematically shows a process for isolating $^{17}$O from water and a $^{17}$O-enriched water production process according to the present disclosure (501: aqueous formaldehyde solution (373 K), 502: formaldehyde photodissociation device (373 K), 503: formaldehyde and water trap device (100 K), 504: methanation device, 505: $^{17}$O-enriched water trap device (243 K), and 506: recirculating the $^{17}$O-enriched water for further concentration)

Hereinafter, embodiments of the present disclosure will be described as follows with reference to the attached drawings. The present disclosure may, however, be exemplified in many different forms and should not be construed as being limited to the specific embodiments set forth herein.

As will be described in detail hereinbelow, a process for isolating an oxygen isotope from water of the present disclosure, due to having excellent isotope selectivity for $^{17}O$, may focus energy solely on $^{17}O$ to isolate the same, thus achieving extremely high energy efficiency, and may enable large-batch production in relatively small-scale facilities.

In detail, a process for isolating an oxygen isotope from water of the present disclosure may include: preparing an aqueous formaldehyde solution by mixing water containing an oxygen isotope with formaldehyde; preparing a vapor mixture containing water vapor and formaldehyde vapor by heating the aqueous formaldehyde solution; and photodissociating the vapor mixture to obtain a gas mixture containing hydrogen and carbon monoxide enriched with the oxygen isotope, water depleted of the oxygen isotope, and residual formaldehyde.

In particular, the oxygen isotope that can be isolated in the present disclosure may be $^{17}O$.

In the preparing an aqueous formaldehyde solution by mixing water containing an oxygen isotope with formaldehyde, the formaldehyde may be mixed in water preferably in a molar ratio in the range of 0.01 to 0.3 with respect to water, more preferably in the range of 0.01 to 0.25, and for example, the formaldehyde may be mixed in water in a molar ratio in the range of 0.05 to 0.2 with respect to water. Mixing with the formaldehyde in an amount less than the lower limit of the above ranges may give rise to insufficient oxygen-isotope exchange reactions, causing an undesirable decrease in productivity, whereas mixing with the formaldehyde in an amount exceeding the upper limit of the above ranges may give rise to an undesirable formation of formaldehyde polymers.

After preparing the aqueous formaldehyde solution, preparing a vapor mixture containing water vapor and formaldehyde vapor heating the aqueous formaldehyde solution may be carried out, wherein the heating may be carried out at a temperature in the range of 320-400 K, preferably in the range of 350-380 K.

The vapor mixture, once obtained, may be photodissociated to produce a gas mixture containing hydrogen and carbon monoxide enriched with the oxygen isotope, water depleted of the oxygen isotope, and residual formaldehyde.

In particular, the photodissociating the vapor mixture may be preferably carried out under a pressure in the range of 1-15 Torr, and for example, may be carried out under a pressure in the range of 5-10 Torr. When the photodissociating the vapor mixture is carried out under a pressure less than the above ranges, it may cause an undesirable decrease in productivity; however, when the photodissociating the vapor mixture is carried out under a pressure greater than the above ranges, photodissociation quantum yield may undesirably decrease to 85% or less.

In particular, according to the present disclosure, an optic fiber laser may be used to irradiate a laser of a particular wavenumber. In particular, the wavenumber of a photodissociating laser for the photodissociating the vapor mixture may be in the range of 28,370-28,400 cm$^{-1}$, preferably in the range of 28,374-28,375 cm$^{-1}$ or in the range of 28396-28398 cm$^{-1}$, more preferably, 28,374.6 cm$^{-1}$, 28,396.3 cm$^{-1}$, 28,397.1 cm$^{-1}$, or a combination thereof, and even more preferably, 28,374.63 cm$^{-1}$, 28,396.32 cm$^{-1}$, 28,397.06 cm$^{-1}$, or a combination thereof.

The photodissociating laser used for the photodissociating the vapor mixture in the present disclosure may be an optic fiber laser with high energy efficiency and simpler maintenance and management, but is not limited thereto. The optic fiber laser contains an active medium inside optic fibers, wherein the medium contains a low-level rare-earth halide. Such an optical fiber laser may be compact in size, light in weight, and convenient in maintenance and management, and particularly, may have high energy efficiency and a broad lasing wavelength region. Accordingly, such an optical fiber laser can be adjusted in intensity (output) across a broad region, and can selectively generate wavenumbers for photodissociation of formaldehyde, and thus may be suitable for use in the present disclosure.

The vapor mixture may be irradiated with a laser of such wavenumbers to selectively photodissociate $^{17}O$-containing formaldehyde. At a formaldehyde transition wavelength used for the photodissociation process, the absorption cross section of $^{17}O$-containing formaldehyde may be in the range of 3.0-3.5 10$^{-19}$ cm$^2$/molecule under a pressure of several Torrs, for example, under 15 Torrs, and the background absorption cross section of the other isotopologues may be in the range of about 8*10$^{-21}$ cm$^2$/molecule, while the isotope selectivity for $^{17}O$ may be about 400.

In the present disclosure, the $^{17}O$-containing water may be heavy water, light water, or a mixture thereof.

In addition, following the obtaining a gas mixture containing hydrogen and $^{17}O$-enriched carbon monoxide, $^{17}O$-depleted water, and residual formaldehyde, isolating the residual formaldehyde by cooling and condensing the $^{17}O$-depleted water and the residual formaldehyde, may be further comprised.

Through the above process, formaldehyde undissociated by the photodissociation process may be collected and discharged, and the photodissociated products produced by photodissociation, hydrogen (H$_2$) and carbon monoxide (CO), may be isolated and collected. Here, the products produced by the photodissociation process, hydrogen and carbon monoxide, and formaldehyde remaining undissociated through the photodissociation process, may be cooled and condensed to be collected. The undissociated formaldehyde, having a freezing point of −92° C., may be cooled below the freezing point to be condensed. Accordingly, it is preferable that the cooling be carried out at a temperature less than or equal to 181 K (−92° C.). For example, the cooling may be carried out at a temperature in the range of 100-181 K.

In particular, since hydrogen and carbon monoxide remain in a gaseous state even under formaldehyde condensation conditions, the photodissociation products, hydrogen and carbon monoxide, may be collected in the gaseous state and then isolated from the formaldehyde.

Since the formaldehyde discharged therefrom may comprise the formaldehyde undissociated during the photodissociation process and possibly containing the oxygen isotope, such formaldehyde may be recirculated to be used in a formaldehyde photodissociation process.

Although as described above, the process for isolating an oxygen isotope from water may be used to collect the oxygen isotope, such a process may be further used to isolate and remove radioactive isotopes. Accordingly, such a process may find suitable applications in the treatment of radioactive carbon wastes.

In detail, the materials used as coolant and structural material of nuclear reactors contain isotopes such as $^{17}O$, and these stable isotopes react with reactor neutrons to form a radioactive isotope, $^{14}C$. Accordingly, if the amount of $^{17}O$ contained in heavy water and the like is reduced to $\frac{1}{10}$ or less, it is possible to reduce $^{14}C$ emissions from heavy water reactors by 90% or more.

However, the carbon monoxide produced by the above-described photodissociation of formaldehyde may contain an isotope of oxygen, $^{17}O$. Accordingly, by performing a catalytic methanation reaction on the photodissociated products containing such carbon monoxide and hydrogen, the isotope of oxygen may be recovered.

According to another aspect of the present disclosure, a process for obtaining $^{17}O$-enriched water may include an operation of obtaining a gas mixture containing hydrogen and $^{17}O$-enriched carbon monoxide, $^{17}O$-depleted water, and residual formaldehyde from $^{17}O$-containing water by the process for isolating $^{17}O$ from water of the present disclosure; and a catalytic methanation operation of adding hydrogen to the gas mixture to induce a catalytic methanation reaction to synthesize methane ($CH_4$) and $^{17}O$-enriched water ($H_2^{17}O$) through methanation.

In detail, once hydrogen and carbon monoxide produced by the photodissociation are isolated and collected, it is preferable that a catalytic methanation reaction 504 be carried out to isolate $^{17}O$ therefrom. Through such a catalytic methanation reaction, water ($H_2O$) and methane ($CH_4$) can be produced from the hydrogen and the carbon monoxide 505, and by condensing and collecting the water thus obtained, $^{17}O$-enriched water can be extracted as a final product.

In other words, by supplying hydrogen to the hydrogen and carbon monoxide produced by the photodissociation, thereby giving rise to a catalytic methanation reaction, water and methane can be produced.

Catalysts that can be used in the catalytic methanation reaction are not limited to any particular material, and may be any one commonly used in the related art. Examples of such catalysts include Raney nickel.

Moreover, the $^{17}O$-enriched water ($H_2^{17}O$) obtained through methanation may be recirculated and used as a starting material for the process for isolating an oxygen isotope from water, to carry out a $^{17}O$-enriched water production process in two stages. In this case, a product enriched with $^{17}O$ isotope to 90% or higher may be obtained.

In other words, to isolate an oxygen isotope, water containing the oxygen isotope may be synthesized 505 through a catalytic methanation reaction from hydrogen and carbon monoxide produced by a first photodissociation process; and additional formaldehyde, not containing the oxygen isotope, may be supplied to the water to induce oxygen isotope exchange reactions between the synthesized water and formaldehyde, to thereby produce formaldehyde containing the oxygen isotope.

Through such oxygen isotope exchange reactions, the oxygen isotope contained in the water enriched through the photodissociation may be transferred to formaldehyde, and accordingly, formaldehyde containing the oxygen isotope may be obtained. Further, the formaldehyde thus obtained, containing the oxygen isotope, may be supplied to a second photodissociation process to be photodissociated, thereby isolating the oxygen isotope therefrom.

Also, the oxygen isotope may be isolated by first producing methane and water containing the oxygen isotope through a catalytic methanation reaction, and then condensing and collecting the water thus produced.

As described above, through two stages of the oxygen isotope isolation process, using the aforementioned process, the concentration factor of the oxygen isotope may be increased up to 30,000.

The process for isolating $^{17}O$ from water according to the present disclosure has selectivity for $^{17}O$ of 400, and can focus energy solely on $^{17}O$ whose abundance ranges from 0.037% to 0.059%, to isolate the same, thus achieving extremely high energy efficiency, and may enable large-batch production in relatively small facilities.

Further, the present disclosure, when applied to the production of $^{17}O$-depleted heavy water to increase cost-effectiveness thereof, may serve to reduce $^{14}C$ formation from heavy water reactors by 90% or more and to dramatically reduce the production costs of $^{17}O$-enriched water, thus enabling various applications of $^{17}O$-enriched water.

Hereinbelow, the present disclosure will be described in greater detail through specific examples. The following examples are examples to assist in an understanding of the present disclosure and are not meant to be restrictive on the scope of the present disclosure.

EXAMPLES

1. Confirmation of Wavelengths for Formaldehyde Photodissociation Useful for $^{17}O$ Isolation Formaldehyde gas ($H_2CO$), when irradiated with 340-360 nm UV light, is photodissociated into hydrogen molecules ($H_2$) and carbon monoxide (CO) as shown in Equation 1.

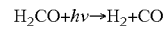

$$H_2CO + h\nu \rightarrow H_2 + CO \qquad \text{Equation 1}$$

Figure 2:
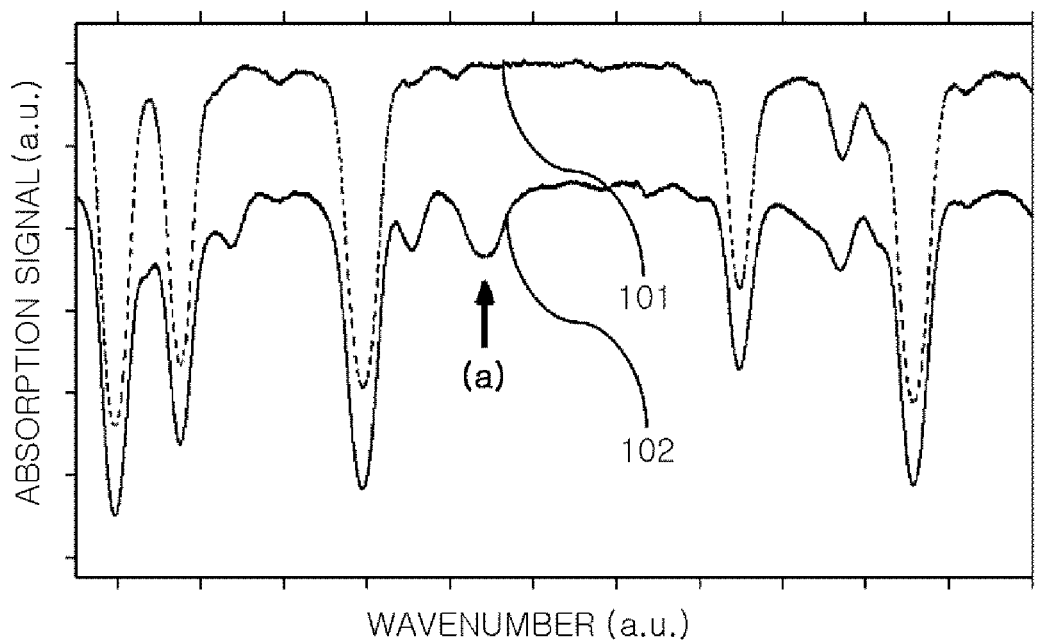
FIG. 2 shows the photodissociation spectrum of formaldehyde around 28,375 cm$^{-1}$ (101: the photodissociation spectrum of formaldehyde containing $^{17}$O in natural isotopic abundance of 0.037%, and 102: the photodissociation spectrum of formaldehyde enriched with $^{17}O$ to 3.8%)
Figure 3:
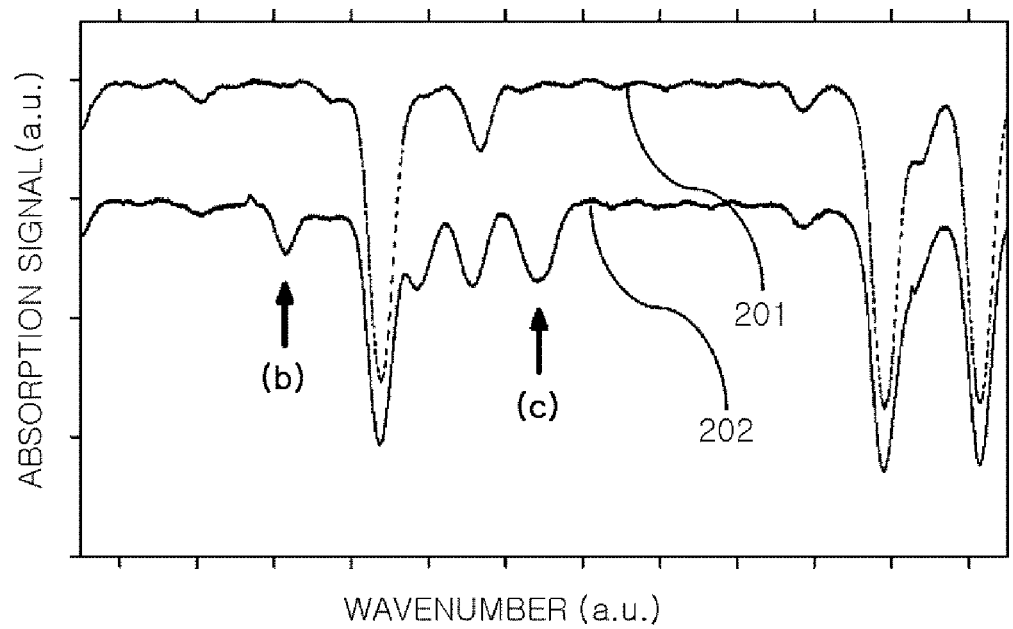
FIG. 3 shows the photodissociation spectrum of formaldehyde around 28,397 cm$^{-1}$ (201: the photodissociation spectrum of formaldehyde containing $^{17}O$ in natural isotopic abundance of 0.037%, and 202: the photodissociation spectrum of formaldehyde enriched with $^{17}O$ to 3.8%)

FIG. 2 and FIG. 3 show the photodissociation spectra of formaldehyde, as measured at 343 K using a narrow-linewidth single mode laser having a linewidth of 60 MHz.

In FIG. 2 and FIGS. 3, 101 and 201 are spectra of formaldehyde containing $^{17}O$ in natural isotopic abundance of 0.037%, and 102 and 202 are photodissociation spectra of formaldehyde containing $^{17}O$ in isotopic abundance of 3.8%. Here, the aqueous formaldehyde solution used contains formaldehyde in a molar ratio of formaldehyde to water of 0.2, the total vapor pressure of the aqueous solution is 15 Torr, and the pressure broadening is about 500 MHz.

(a) shown in FIG. 2, and (b) and (c) shown in FIG. 3 are photodissociation wavelengths useful for $^{17}O$ isolation, wherein wavenumbers of the respective photodissociating lasers are 28,374.63 cm$^{-1}$, 28,396.32 cm$^{-1}$, and 28,397.06 cm$^{-1}$, respectively. In (a) shown in FIG. 2, and (b) and (c) shown in FIG. 3, the absorption cross section of $^{17}O$ formaldehyde was 3.0-3.5×10$^{-19}$ cm$^2$/molecule, the background absorption cross section of the other isotopologues was about 8×10$^{-21}$ cm$^2$/molecule, and the selectivity for $^{17}O$ was about 400.

In particular, isotope selectivity S is defined by Equation 2 below, where $C_F$ is a $^{17}O$ isotopic abundance of the starting material, and $C_P$ is a $^{17}O$ isotopic abundance of the product.

$$S = \frac{C_P/(1-C_P)}{C_F/(1-C_F)} \qquad \text{Equation 2}$$

Figure 4:
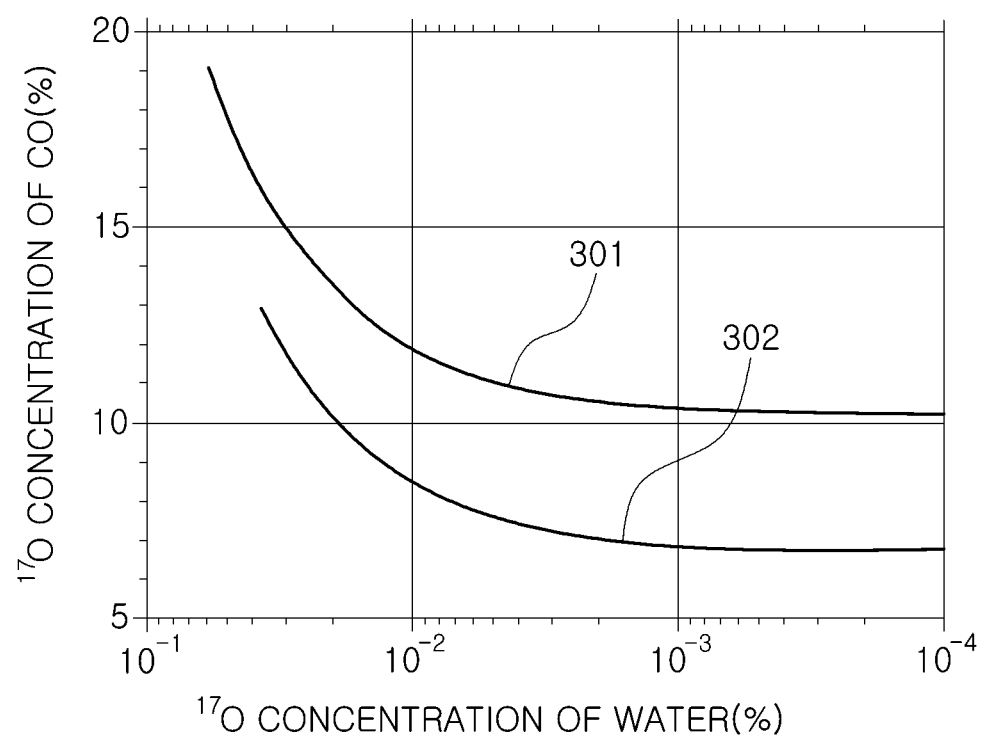
FIG. 4 shows the relationship between the $^{17}O$ concentration (abundance) of a photodissociated product (CO) and the $^{17}O$ concentration (abundance) in tail water, in a $^{17}O$ isolation process with selectivity for $^{17}O$ of 400 (301: heavy water enriched with $^{17}O$ to 0.059%, and 302: light water enriched with $^{17}O$ to 0.037%).

2. Relationship Between the $^{17}O$ Abundance in Photodissociated Product and the ($^{17}O$) Abundance in Tail Water FIG. 4 shows the relationship between the concentration of a photodissociated product and a component ratio in tail water in an isolation process having selectivity for $^{17}O$ of 400.

The graph 301 is the case of heavy water with an $^{17}O$ abundance of 0.059%, and the graph 302 is the case of light water with an $^{17}O$ abundance of 0.037%. In a process of removing $^{17}O$ isotope from heavy water to 0.005%, the isotopic abundance of $^{17}O$ in the photodissociated product, carbon monoxide, becomes 11%. In a process of concentrating $^{17}O$, using light water as a starting material, when the $^{17}O$ isotopic abundance in tail water is 0.02%, an $^{17}O$ product having enriched isotopic abundance to 10% may be obtained, whereas if another isolation process is added to carry out the process in two stages, an $^{17}O$ product having enriched isotopic abundance up to 90% or higher may be obtained.

Example 1

Isolation of Oxygen Isotope from Water

An aqueous formaldehyde solution 501 prepared by dissolving formaldehyde in heavy water in a molar ratio of 0.2 or less to water was heated to 343 K, and vapor of heavy water and formaldehyde generated thereby was injected into a photodissociation device 502 to a pressure about 5-15 Torr. Inside the photodissociation device 502, being heated at 343 K, $^{17}O$ formaldehyde is photodissociated, and at the same time, oxygen-isotope exchange reactions such as that shown in Equation 3, take place between residual formaldehyde and heavy water.

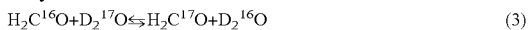

$$H_2C^{16}O + D_2{}^{17}O \rightleftarrows H_2C^{17}O + D_2{}^{16}O \qquad (3)$$

Although the oxygen-isotope exchange reactions occur within a few minutes, hydrogen-deuterium exchange reactions are extremely slow, having a reaction time spanning a few hundred hours, and thus, during $^{17}O$ isolation processes, hydrogen isotopes are not exchanged. Accordingly, there is no loss of heavy water serving as the starting material, in $^{17}O$ removal processes.

In particular, the $^{17}O$ -depleted heavy water ($D_2O$) in which $^{17}O$ has been depleted to 0.005% or less, is trapped in a water-trap device 503 and becomes the final product. The residual formaldehyde is trapped in a liquid nitrogen-trap maintained at 100 K, and is thereby isolated from syngas ($H_2 + C^{17}O$), a photodissociated product. If necessary, the syngas may be transferred to a methanation device 504 to which hydrogen is additionally supplied, to produce $^{17}O$-enriched water enriched to about 10% 505 as a byproduct.

Through the above-described processes, $^{17}O$ contained in the heavy water was depleted to produce $^{17}O$ -free heavy water ($D_2O$).

Example 2

Production of $^{17}O$ -Enriched Water

An aqueous solution 501, prepared by dissolving formaldehyde in water in a molar ratio of about 0.1-0.2 was heated to 373-393 K, and vapor of the aqueous formaldehyde solution generated thereby was injected into a photodissociation device 502 to a pressure of about 5 Torr. Inside the photodissociation device 502 being heated at 373 K, $^{17}O$ formaldehyde is photodissociated, and at the same time, oxygen-isotope exchange reactions take place between formaldehyde and water.

Residual formaldehyde and water, remaining after the photodissociation, are trapped in a liquid-nitrogen trap maintained at 100 K and thereby isolated from syngas, which is a photodissociated product. The syngas is transferred to a methanation device 504 to which hydrogen is additionally supplied, to be transformed into $^{17}O$ -enriched water enriched to about 10% 505.

A recirculation line 506 may be provided for a second stage process. In the second stage, an aqueous solution 501 prepared by dissolving formaldehyde in 10% $^{17}O$ -enriched water in a molar ratio of about 0.1-0.2, may be used. The isolation process including two stages may produce $^{17}O$ -enriched water enriched to 90% or higher.

Through the processes as set forth above, $^{17}O$ -enriched water may be produced using water as the starting material.

As set forth above, according to the examples, a process for isolating $^{17}O$ from water, having selectivity for $^{17}O$ of 400, may focus energy solely on $^{17}O$ with an abundance of 0.059%, to isolate the same, thus achieving extremely high energy efficiency, and may enable large-batch production in relatively small-scale facilities. Further, the present disclosure may be applied to the production of $^{17}O$ -depleted heavy water to increase the cost-effectiveness thereof, may reduce $^{14}C$ formation from heavy water reactors by 90% or more, and may dramatically reduce the production cost of $^{17}O$ -enriched water, thus enabling various applications of $^{17}O$ -enriched water.

While exemplary embodiments have been shown and described above, it will be apparent to those skilled in the art that modifications and variations could be made without departing from the scope of the present invention, as defined by the appended claims.

What is claimed is:

1. A process for isolating $^{17}O$ from water, comprising:
preparing an aqueous formaldehyde solution by mixing $^{17}O$ -containing water with formaldehyde;
preparing a vapor mixture containing water vapor and formaldehyde vapor by heating the aqueous formaldehyde solution; and
obtaining $^{17}O$-depleted water, residual formaldehyde, and a gas mixture containing hydrogen and $^{17}O$ -enriched carbon monoxide, through photodissociating the vapor mixture,
wherein a wavenumber of a photodissociating laser for the photodissociating the vapor mixture is in a range of 28,370-28,400 cm$^{-1}$.

2. The process for isolating $^{17}O$ from water of claim 1, wherein the formaldehyde is mixed with water in a molar ratio of formaldehyde to water in a range of 0.01-0.3.

3. The process for isolating $^{17}O$ from water of claim 1, wherein the heating is carried out at a temperature in a range of 320-400 K.

4. The process for isolating $^{17}O$ from water of claim 1, wherein the photodissociating the vapor mixture is carried out under a pressure in a range of 1-15 Torr.

5. The process for isolating $^{17}O$ from water of claim 1, the wavenumber of a photodissociating laser for the photodissociating the vapor mixture is 28,374.63 cm$^{-1}$, 28,396.32 cm$^{-1}$, 28,397.06 cm$^{-1}$, or a combination thereof.

6. The process for isolating $^{17}O$ from water of claim 1, wherein the photodissociating laser used for the photodissociating the vapor mixture is an optic fiber laser.

7. The process for isolating $^{17}O$ from water of claim 1, wherein the $^{17}O$-containing water is heavy water, light water, or a mixture thereof.

8. The process for isolating $^{17}O$ from water of claim 1, further comprising, following the obtaining, $^{17}O$-depleted water, residual formaldehyde, and a gas mixture containing hydrogen and $^{17}O$-enriched carbon monoxide, cooling and condensing them separate O-depleted water and the residual formaldehyde from the gas mixture containing hydrogen and $^{17}O$-enriched carbon monoxide.

9. The process for isolating $^{17}O$ from water of claim 8, wherein the cooling is carried out at a temperature less than or equal to 181 K (−92° C.).

10. A process for producing $^{17}O$-enriched water, comprising:
   an operation of obtaining $^{17}O$-depleted water, residual formaldehyde, and a gas mixture containing $^{17}O$-enriched carbon monoxide and hydrogen, from $^{17}O$-containing water by the process for isolating $^{17}O$ from water of claim 1; and
   a catalytic methanation operation of adding hydrogen to the gas mixture to induce a catalytic methanation reaction to synthesize methane ($CH_4$) and $^{17}O$-enriched water ($H_2^{17}O$) through methanation.

11. The process for producing $^{17}O$-enriched water of claim 10, wherein the $^{17}O$-enriched water ($H_2^{17}O$) obtained through methanation is recirculated as a starting material for the process for isolating $^{17}O$ from water, to carry out a $^{17}O$-enriched water production process in two stages.

* * * * *